(12) United States Patent
Khetani et al.

(10) Patent No.: US 6,962,997 B1
(45) Date of Patent: Nov. 8, 2005

(54) PROCESS AND INTERMEDIATES FOR RESOLVING PIPERIDYL ACETAMIDE STEROISOMERS

(75) Inventors: Vikram Khetani, Jersey City, NJ (US); Yalin Luo, New Providence, NJ (US); Sowmianarayanan Ramaswamy, Bridgewater, NJ (US)

(73) Assignee: Celgene Corporation, Summit, NJ (US)

(*) Notice: Subject to any disclaimer, the term of this patent is extended or adjusted under 35 U.S.C. 154(b) by 0 days.

(21) Appl. No.: 09/283,645

(22) Filed: Apr. 1, 1999

Related U.S. Application Data

(63) Continuation of application No. 08/861,988, filed on May 22, 1997, now Pat. No. 5,936,091.

(51) Int. Cl.$^7$ ............................................. C07D 211/32
(52) U.S. Cl. ................................................... 546/233
(58) Field of Search ................................. 546/233, 223

(56) References Cited

U.S. PATENT DOCUMENTS

| | | | |
|---|---|---|---|
| 2,507,631 A | 5/1950 | Hartmann et al. | 546/185 |
| 2,957,880 A | 10/1960 | Rometsch | 546/233 |
| 4,410,700 A | * 10/1983 | Rice | 546/149 |
| 5,936,091 A | * 8/1999 | Khetani et al. | 546/233 |

OTHER PUBLICATIONS

Jursic et al. "determination of enantiomeric composition of 1–phenyl . . . " Tetrahedron:assymetry, v/5 1711–1716 (1994).*
Patrick et al. "Synthesis of deuterium . . . " J. Label. Pharm. v.9, 485–490 (1982).*
Berrang et al. "Enantiomeric aminopropiophenones" Ca 97:38738 (1982).*
Ohashie et al. "Acylaminonaphthaniene . . . " CA 104:186157 (1985).*
Banderplas et al. "A convenient synthesis of . . . " CA 118:101538 (1992).*
Jursic et al. "Determination of enantiomeric composition of 1–phenyl–2(2–piperidinyl–acetamide" Tetrahedron:asymmetry v/5, 1711–1716 (1994).*
Patrick et al. "Synthesis of deuterium labelled methylphenidate . . . " J. Label. Pharm. v.9, p. 485–490 (1982).*
Berrang et al. "Enantiomeric aminopropiophenones" CA 97:38738 (1982).*
Ohashie et al. "Acylaminonaphthanlene derivatives" CA 104:186157 (1985).*
Feng et al. "molecular determinants of the platelet . . . " CA 117:111440, 1992.*
Morrison and Byd "Orgainc Chemistry" Allyn and Bacon, 1973, p. 32–34.*
CAS RN 6051–31–6 or RN 3019–58–7.*
Vanderplas et al. "A convenient synthesis of cis–benayl–hydroxymethyl cyclohexylamine" CA 118:101538 (1992).*

Dobashi et al. "Entioselectivity of hydrogen bond . . . " CA 106:66522, 1986.*
Japan Chem Soc. "Organic Reaction" v. 1, No. 18, p. 504–505 (translation attached), 1958.*
Brown, G., "The use of methylphenidate for cognitive decline associated with HIV disease," *Int'l J. Psychiatry Med.*, 1995, 25(1), 21–37.
Greenhill, L., "Attention–deficit hyperactivity disorder," *Child & Adol. Psych. Clin. N.A.*, 1995, 4(1), 123–168.
Phashi, et al., "Acyl(amino)naphthanlene derivatives," CA104:186157, 1985.
Aoyama, T., et al., "Nonlinear kinetics of threo–methylphenidate enantiomers in a patient with narcolepsy and in healthy volunteers," *Eur. J. Clin. Pharmacol.*, 1993, 44, 79–84.
Barkley, R. A., et al., "The adolescent outcome of hyperactive children diagnosed by research criteria: I. An 8–year prospective follow–up study," *J. Am. Acad. Adolesc. Psychiatry.*, 1990, 29(4), 546–557.
Bruera, E., and Neumann, C.M., "The uses of phychotropics in symptom management in advanced cancer," *Phycho–Oncology.*, 1998, 7, 346–358.
Garland, E. J., "Pharmacotherapy of adolescent attention deficit hyperactivity disorder: challenges, choices and caveats," *J. Physchopharmacology.*, 1998, 12(4), 385–395.
Golden, G. S., "Role of attention deficit hyperactivity disorder in learning disabilities," *Seminars in Neurology.*, 1991, 11(1), 35–41.
Goldman, L. S., et al., "Diagnosis and treatment of attention–deficit/hyperactivity disorder in children and adolescents," *J. Am. Med. Assn.*, 1998, 279(14), 1100–1107.
No author, "*Methylphenidate hydrochloride*," Environmental Health Perspectives, 1997, 105 (supp 1), 319.
Patrick, K. S., et al., "Pharmacology of the enantiomers of threo–methylphenidate," *J. Pharmacol. Expt. Ther.*, 1987, 241, 152–158.
Spencer, T., et al., "Pharmacotherapy of attention–deficit hyperactivity disorder across the life cycle," *J. Am. Acad. Adolesc. Psychiatry.*, 1996, 35(4), 409–432.
Shrinvas, N. R., et al., "Enantioselective pharmacokinetics and pharmacodynamics of d,l–threo–methylphenidate in children with attention deficit hyperactivity disorder," *Clin. Pharmacol, Ther.*, 1992, 52(5), 561–568.
Stein, M.A., et al., "Methylphenidate dosing: Twice daily versus three times daily,"*Pediactrics.*, 1996, 98(4), 748–756.
Swanson, J. M., et al., "Analog classroom assessment of Adderall in children with ADHD,"*J. Am. Acad Child Adolesc. Psychiatry.*, 1998, 37(5), 519–525.

(Continued)

*Primary Examiner*—Ceila Chang
(74) *Attorney, Agent, or Firm*—Woodcock Washburn LLP

(57) ABSTRACT

Processes and intermediates for preparing 2-substituted piperidines such as 2-substituted d-threo piperidines are provided, including processes and intermediates for resolution of piperidyl acetamide stereoisomers.

12 Claims, No Drawings

OTHER PUBLICATIONS

Ward, M. F., et al., "The Wender Utah rating scale: an aid in the retrospective diagnosis of chilhood attention deficit hyperactivity disorder," *Am. J. Phychiatry.*, 1993, 150(6), 885–890.

Zametkin, A. J. and Ernst, M., "Problems in the management of attention–deficit/hyperactivity disorder," *New. Eng. Jour. Med.*, Jan. 1999, 340(1), 40–46.

\* cited by examiner

PROCESS AND INTERMEDIATES FOR RESOLVING PIPERIDYL ACETAMIDE STEROISOMERS

This is a continuation of Ser. No. 08/861,988 filed May 22, 1997 now U.S. Pat. No. 5,936,091.

FIELD OF THE INVENTION

This invention is directed to novel processes for resolution of piperidyl acetamide stereoisomers. The invention additionally is directed to synthetic intermediates and reaction products useful in such processes.

BACKGROUND OF THE INVENTION

Substituted piperidines have found use in the treatment of many nervous system disorders. For example, methylphenidate has been used to treat Attention Deficit Disorder (ADD), Attention Deficit Hyperactivity Disorder (ADHD) and cognitive decline in Acquired Immunodeficiency Syndrome (AIDS) and AIDS Related Complex (ARC) patients. (See, e.g., Greenhill, *Child & Adol. Psych. Clin. N.A.*, 1995, 4, 123, and Brown, *Intl. J Psychl. Med.*, 1995, 25, 21).

Many currently available synthetic routes to methylphenidate and other substituted piperidines involve preparation of racemic mixtures. (See, e.g., U.S. Pat. No. 2,507,631, to Hartmann, et al., and U.S. Pat. No. 2,957,880, to Rometsch, et al.). There are, however, a number of disadvantages associated with racemic mixtures of such drugs. Current administration of racemic methylphenidate often results in notable side effects such as anorexia, weight loss, insomnia, dizziness and dysphoria. Additionally, racemic methylphenidate produces a euphoric effect when administered intravenously or through inhalation, and thus carries a high potential for substance abuse in patients.

U.S. Pat. Nos. 2,507,631 and 2,957,880 disclose synthetic procedures wherein methylphenidate, alternatively known as methyl α-piperid-2-ylphenylacetate, is prepared through a multi-step process in which 2-chloropyridine and phenylacetonitrile initially are coupled to form α-pyrid-2-ylphenylacetonitrile. The resulting α-pyrid-2-ylphenylacetonitrile then is hydrated in the presence of acid to yield α-pyrid-2-ylphenylacetamide which, in turn, is either: (a) catalytically hydrogenated to yield α-piperid-2-ylphenylacetamide and then converted to methyl α-piperid-2-ylphenylacetate, or (b) converted to methyl a-pyrid-2-ylphenylacetate which, in turn, is hydrogenated to yield methyl α-piperid-2-ylphenylacetate.

In the first embodiment of U.S. Pat. No. 2,507,631 and in the process described in U.S. Pat. No. 2,957,880, α-piperid-2-ylphenylacetamide is first separated into the threo and erythro diastereomeric racemates. This is accomplished through evaporation of the solvent utilized in the hydrogenation (i.e., acetic acid), addition of sodium hydroxide to precipitate the α-piperid-2-ylphenylacetamide free base, recrystallization of this amide from ethyl acetate, and preferential crystallization of the erythro form by passing gaseous hydrogen chloride through an ethanolic solution of the amide.

The isolated erythro racemate then is resolved through formation of the l-tartrate salt, repeated recrystallizations of this salt from 96% ethanol are performed until a constant rotation is obtained, and the l-erythro form of α-piperid-2-ylphenylacetamide is precipitated with sodium hydroxide. The l-erythro form of α-piperid-2-ylphenylacetamide thus obtained is said to be subjected to epimerization to yield the desired d-threo diastereomer of α-piperid-2-ylphenylacetamide through treatment with 6 M potassium hydroxide. According to the disclosed procedure, the α-piperid-2-ylphenylacetamide thus obtained is converted to d-threo methyl α-piperid-2-ylphenylacetate through hydrolysis and esterification.

Some in the art have raised doubts as to whether the procedures disclosed in U.S. Pat. Nos. 2,507,631 and 2,957,880 do, in fact, produce the desired d-threo isomer. Indeed, J. R Soares, "Steroochemical Studies On Potential Central Nervous System Active Agents and Studies On The Chemistry Of Some 3-Benzoylpiperidines," 1971, Columbia University Ph.D. dissertation, p. 115, discloses that "all attempts to epimerize the resolved erythro-amides to the corresponding threo-amides by the procedure outlined in [U.S. Pat. No. 2,957,880] failed completely."

In any event, the synthetic procedure described in U.S. Pat. Nos. 2,507,631 and 2,957,880 is wasteful in that it involves discarding the threo α-piperid-2-ylphenylacetamide racemate which is isolated following the recrystallization step and which typically represents approximately 25% of the acetamide product obtained via hydrogenation.

Consequently, there remains a need in the art for alternative synthetic procedures for the preparation of methylphenidate and other substituted piperidines. In particular, there is a need for synthetic procedures that do not require separating and discarding threo stereoisomers from the hydrogenation reaction product.

OBJECTS OF THE INVENTION

It is an object of the present invention to provide processes for the preparation of substituted piperidines.

It is another object of this invention to provide processes that provide synthetic intermediates and, hence, products having high optical purity.

It is yet another object to provide processes that proceed more efficiently than the processes disclosed by the prior art.

SUMMARY OF THE INVENTION

These and other objects are satisfied by the present invention, which provides processes and intermediates for preparing piperidyl acetamides. In preferred embodiments, the processes of the invention comprise reacting d,l-threo piperidyl acetamide stereoisomers having formulas IIa and IIb:

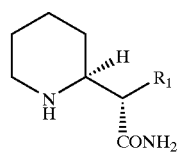

l-threo

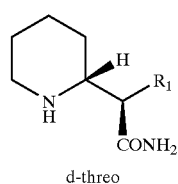

d-threo ($R_1$=aryl having about 6 to about 28 carbon atoms) with an acid resolving agent in an organic solvent, thereby forming acid salts of the d-threo stereoisomers preferentially with respect to the l-threo stereoisomers. The resulting acid salts then are reacted with aqueous base to form the corresponding piperidyl acetamide, which subsequently is converted to a corresponding ester.

DETAILED DESCRIPTION OF THE INVENTION

This invention provides novel processes for stereoselective synthesis of a variety 2-substituted piperidine stereoisomers. In one aspect, the invention is directed to synthetic methods involving hydrogenation of pyridines having formula I:

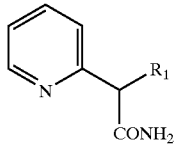

I wherein $R_1$ is aryl having about 6 to about 28 carbon atoms. Aryl groups, as used herein, are aromatic groups containing a delocalized π-electron cloud. Such aromatic groups can be substituted with one or more substituents, such as, for example, halo, alkyl, aryl, hydroxy, alkoxy, carboxy, and cycloalkyl. Exemplary aryl groups include phenyl, naphthyl, xylyl, chlorophenyl, fluorophenyl, trifluoromethylphenyl, and bromophenyl. Phenyl groups are preferred.

This hydrogenation can be effected by any of the numerous techniques known in the art. One preferred hydrogenation technique involves reacting the pyridine with hydrogen gas in the presence of a suitable catalyst in an alkanoic acid having 1 to about 10 carbon atoms. The hydrogenation preferably run at 25° C. and 40 psi. Representative catalysts contain platinum, with platinum oxide being particularly preferred. One preferred alkanoic acid is acetic acid.

Hydrogenation of pyridine I provides a mixture of piperidine diastereomers IIa–d:

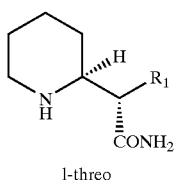

IIa l-threo

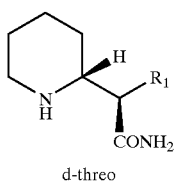

IIb d-threo

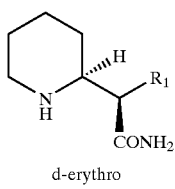

IIc d-erythro

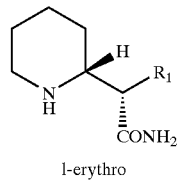

IId l-erythro

In accordance with the present invention, this mixture is treated with an organic base in an organic solvent to epimerize the erythro stereoisomers into threo forms. The epimerization can, for example, be effected in an aromatic hydrocarbon solvent such as toluene using an alkali metal alkoxide such as potassium tert-butoxide. In preferred embodiments, the epimerization is effected at 70 ° C. in an aromatic hydrocarbon solvent such as toluene using two equivalents of an alkali metal alkoxide such as potassium tert-butoxide.

The resulting composition, which should consist predominantly of d,l-threo piperidyl acetamide steoisomers, is reacted with an acid resolving agent in an organic solvent, thereby forming acid salts of the d-threo stereoisomers preferentially with respect to the l-threo stereoisomers. Alkyl groups according to the invention are hydrocarbons which are straight, branched, or cyclic. Such hydrocarbons can be substituted with one or more substituents, such as, for example, halo, hydroxy, alkoxy, and carboxy groups. Exemplary alkyl groups include methyl, ethyl, isopropyl, n-butyl, t-butyl, n-pentyl, acetyl, trifluoromethyl, chloromethyl, and hexyl groups. Representative solvents include alcohols, alkyl alkanoates (e.g., ethyl acetate), ketones (e.g., acetone), and ethers (e.g., tetrahydrofuran, dioxane). Preferred solvents are alcohols having 1 to about 5 carbon atoms, include branched and straight chain compounds such as ethyl, propyl and tert-butyl alcohol, with isopropanol being particularly preferred. The reaction of piperidyl acetamide stereoisomers with acid resolving agents preferably is performed with stirring at room temperature.

Representative acid resolving agents include L-(+)- or D-(−)-tartaric acid, dipivaloyl-D-tartaric acid, (1S)-(+)-10-camphorsulphonic acid, L-(−)-malic acid, (S)-(+)-mandelic acid, N-acetyl-l-aspartic acid (and other N-protected amino acids), (R)-(+)-1,1'-bi-s-napthol, (+)-camphoric acid, D-glucuronic acid, and derivatives thereof. Those believed to be useful for forming d-threo stereoisomers preferentially with respect to l-threo isomers include (+)-dibenzoyl-D-tartaric acid. Derivatives of D-(−)-tartaric acid are preferred, including those having formula (III):

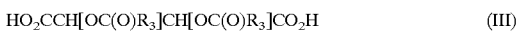

$$HO_2CCH[OC(O)R_3]CH[OC(O)R_3]CO_2H \quad (III)$$

where each $R_3$, independently, is aryl having 6 to about 28 carbon atoms or aralkyl having 7 to about 28 carbon atoms. Aralkyl groups according to the invention are those (such as, for example, benzyl groups, which both aryl and alkyl portions and are covalently bound to a core molecule (such as the above-noted carbonyl-functionalized tartaric acid) through the alkyl portions thereof.

In certain alternative embodiments of the invention, the piperidyl acetamide stereoisomers having formulas IIa and IIb are reacted with an acid resolving agent in an organic solvent to form acid salts of the l-threo stercoisomers preferentially with respect to the d-threo stereoisomers. Resolving agents believed to be useful for forming l-threo stereoisomers preferentially with respect to d-threo isomers include (−)dibenzoyl-L-tartaric acid. Derivatives of L-(−)- tartaric acid are preferred, including those having formula (III). Crystallization preferably is performed at ambient temperature.

The acid salts obtained via resolution typically are dissolved in water and treated with an aqueous base such as a carbonate, bicarbonate, or hydroxide to precipitate the corresponding piperidyl amide free base in substantially pure form. They then can be reacted with an alcohol having, for example, 1 to about 5 carbon atoms in the presence of acid to form the corresponding ester.

Additional objects, advantages, and novel features of this invention will become apparent to those skilled in the art upon examination of the following examples thereof, which are not intended to be limiting.

EXAMPLE 1

Preparation of d-Threo-methylphenidate Hydrochloride Via Diastereomeric Separation and Resolution of d,l-erythro-Amide (Comparative Example)

A. α-Phenyl-α-pyridyl-(2)-acetonitrile

| Materials: | |
| --- | --- |
| 2-Chloropyridine (99%) | 286 g (2.50 moles) |
| Benzyl cyanide (98%) | 314 g (2.62 moles) |
| Sodium amide (90%) | 217 g (5.00 moles) |
| Toluene | 0.98 + 0.17 L |
| Water | 0.87 L |
| Ethyl acetate | 0.43 L |
| Hexanes | 1.56 + 1.95 L |
| Brine | 0.43 L |

Procedure

A 5 L multi-neck glass reactor was charged with 2-chloropyridine, benzyl cyanide, and toluene (0.98 L). Sodium amide powder was added over a 1 h period via a solid-addition funnel, keeping the reaction temperature below 30° C. The reaction mixture was stirred for 16 h at ambient temperature. The reaction was then cooled to ~10° C., and quenched with 0.87 L water. Ethyl acetate (0.43 L) was added to solubilize the precipitated product. The organic layer was separated and washed once with 0.43 L brine. Solvent was removed from the organic layer on a rotovap, and toluene (0.17 L), followed by hexanes (1.56 L), were added to the resulting residue. The resulting slurry was filtered. The filter cake was washed with hexanes (1.95 L), and dried to give 441 g of α-phenyl-α-pyridyl(2)-acetonitrile as light brown crystals (90% yield based on 2-chloropyridine).

B. α-Phenyl-α-pyridyl-(2)-acetamide

| Materials: | |
| --- | --- |
| α-Phenyl-α-pyridyl-(2)-acetonitrile | 441 g (2.27 moles) |
| Conc. $H_2SO_4$ | 0.55 L |
| Water | 1.63 L |
| 50% NaOH | 1.27 L |

Procedure

The reactor was charged with conc. $H_2SO_4$, and cooled to ~10° C. α-Phenyl-α-pyridyl-(2)-acetamide (from Example 1.A) was added portionwise, keeping the temperature below 30° C. The reaction was stirred at ambient temperature for 16 h. The reaction mixture then was cooled to 10° C., at which point water was added. The NaOH then was added to a pH of 12, keeping the temperature below 30° C. The resulting crystals were filtered, and the filter cake was washed with water and dried under vacuum to give 482 g (100%) of α-phenyl-α-pyridyl-(2)-acetamide.

$NH_4OH$ can be substituted for NaOH to adjust the pH to 12. One advantage of using $NH_4OH$ is that the by-product that is formed (ammonium sulfate) is more soluble in water then the by-product (sodium sulfate) formed when NaOH is used as the base. Thus, the product crystals are less likely to be contaminated with inorganic salts.

C. d,l-erythro-α-Phenyl-α-piperidyl-(2)-acetamide

| Materials: | |
| --- | --- |
| α-Phenyl-α-pyridyl-(2)-acetamide | 482 g (2.27 moles) |
| Platinum oxide ($PtO_2$) | 8.06 g |
| Acetic acid | 1.68 + 4.13 L |
| Celite | 500 + 250 g |
| Ethyl acetate | 3.10 + 0.62 + 2.07 + 2.07 + 4.13 + 0.21 L |
| Water | 4.13 + 1.03 + 2.07 L |
| 50% NaOH | 0.56 L |

Procedure

The reactor was charged with α-phenyl-α-pyridyl-(2)-acetamide (from Example 1.B), acetic acid (1.68 L), and $PtO_2$. The reactor then was filled with hydrogen gas, and pressurized to 60 psi. The reaction mixture was hydrogenated at room temperature for 16 h. The reaction mixture was filtered through a pad of Celite (500 g) to remove catalyst, and the Celite pad washed with acetic acid (4.13 L). The filtrate was concentrated under reduced pressure. Ethyl acetate (3.10 L) was added to the residue and stirred for 2 h. The resulting crystals (first crop) were filtered, washed with ethyl acetate (0.62 L), and dried. The filtrate was concentrated under reduced pressure. Ethyl acetate (2.07 L) was added to the residue and stirred for 2 h. The resulting crystals (second crop) were filtered, washed with ethyl acetate (2.07 L), and dried. The crystals from first and second crops were combined and dissolved in water (4.13 L), filtered through a pad of Celite (250 g), and the Celite pad was washed with water (1.03 L). The resulting filtrate was cooled to 10° C., followed by addition of 50% NaOH until the pH of the mixture was 13 and the free amine crystallized out. The crystals were filtered, washed with water (2.07 L), and dried to give 297 g (60%) of d,l-erythro-α-phenyl-α-piperidyl2)-acetamide.

D. l-erythro-α-Phenyl-α-piperidyl-(2)-acetamide

| Materials: | |
| --- | --- |
| d,l-erythro-α-phenyl-α piperidyl-(2)-acetamide | 297.2 g (1.361 moles) |
| D-(-)-Tartaric acid | 204.3 g (1.361 moles) |
| Methanol | 7.13 + 7.13 L |
| Water | 2.0 L |
| 50% NaOH | 0.1 L |

Procedure

D-(−)-Tartaric acid dissolved in methanol (7.13 L) was added to a stirred solution of d,l-erythro-α-phenyl-d-piperidyl-(2)-acetamide (from Example 1.C), dissolved in methanol (7.13 L). The resulting clear solution was stirred for 16 h, whereby the tartrate salt of l-erythro-acetamide crystallized out. The crystals were filtered, washed with methanol and dried. This tartrate salt was dissolved in water and 50% NaOH was added to a pH of 12, whereby the free base precipitated out. The precipitated crystals were filtered, washed with water and dried to give 119 g (40%) of l-erythro-α-phenyl-α-piperidyl-2)-acetamide.

E. d-threo-α-Phenyl-α-piperidyl-(2)-acetamide

| Materials: | |
|---|---|
| l-erythro-α-phenyl-α-piperidyl-(2)-acetamide | 119 g (0.544 moles) |
| Potassium t-butoxide (95%) | 141.5 g (1.198 moles) |
| Toluene | 3.57 L |
| Water | 0.60 + 0.30 + 1.20 L |
| Conc. HCl | 0.24 + 0.12 L |
| 50% NaOH | 0.14 L |

Procedure

A mixture of l-erythro-α-phenyl-α-piperidyl-(2)-acetamide (from Example 1.D), potassium t-butoxide, and toluene was heated to 70° C. and stirred for 16 h. The reaction mixture was cooled to room temperature, followed by slow addition of water (0.60 L). Conc. HCl (0.24 L) was added to this resulting mixture, and stirred for 0.5 h. The layers were separated, and the top organic layer was washed with a prepared solution of conc. HCl (0.12 L) and water (0.30 L). The combined aqueous layers were cooled to 10° C., and 50% NaOH was added to a pH of 12, whereby the free base precipitated out. The crystals were filtered, washed with water (1.20 L), and dried to give 101 g (85%) of d-threo-α-phenyl-α-piperidyl-(2)-acetamide.

F. d-threo-Methylphenidate Hydrochloride

| Materials: | |
|---|---|
| d-threo-α-phenyl-α-piperidyl-(2)-acetamide | 101 g (0.46 moles) |
| Conc. H$_2$SO$_4$ | 121 mL |
| Methanol | 1.1 L |
| Water | 0.81 L |
| 50% NaOH | 175 mL |
| Diethyl ether | 1.0 + 1.0 + 1.0 + 1.0 L |
| Magnesium sulfate | 20 g |
| HCl gas | As needed. |

Procedure

A solution of d-threo-α-phenyl-α-piperidyl-(2)-acetamide (from Example 1.E) and conc. H$_2$SO$_4$ in methanol was heated to reflux and stirred for 2 days. The reaction mixture was cooled to room temperature and concentrated under reduced pressure. Water (0.81 L) and ether (1.0 L) were added to the residue. NaOH was added to a pH of 12, and the layers were separated. The aqueous layer was extracted with ether (1.0 L). MgSO$_4$ was added to the combined ether layers, filtered, and washed with ether (1.0 L). HCl gas was passed through the filtrate with stirring, whereby white crystals of d-threo-methylphenidate hydrochloride precipitated out. The crystals were filtered, washed with ether (1.0 L), and dried to give 100 g (80%) of d-threo-methylphenidate hydrochloride.

The overall yield for Example 1 was 14.7%.

EXAMPLE 2

Preparation of d-Threo-methylphenidate Hydrochloride Via Epimerization and Resolution of d,l-Threo-amide Enantiomers A. α-Phenyl-α-pyridyl-2-acetonitrile

| Materials: | |
|---|---|
| 2-Chloropyridine (99%) | 172 g (1.50 moles) |
| Benzyl cyanide (98%) | 188 g (1.576 moles) |
| Sodium amide (90%) | 130 g (3.00 moles) |
| Toluene | 0.59 + 0.10 L |
| Water | 0.52 L |
| Ethyl acetate | 0.26 L |
| Hexanes | 0.94 + 1.17 L |
| Brine | 0.26 L |

Procedure

The reactor was charged with 2-chloropyridine, benzyl cyanide, and toluene (0.59 L). Sodium amide powder was added over a 1 h period via a solid-addition funnel, keeping the reaction temperature below 300° C. The reaction mixture was stirred for 16 h at ambient temperature. The reaction was cooled to ~10° C., and quenched with 0.52 L water. Ethyl acetate (0.26 L) was added to solubilize the precipitated product. The organic layer was separated and washed once with 0.26 L brine, and solvent was removed from the organic layer on a rotovap. Toluene (0.10 L), followed by hexanes (0.94 L) were added to the resulting residue. The resulting slurry was filtered, and the filter cake was washed with hexanes (1.17 L), and dried to give 265 g of α-phenyl-α-pyridyl-(2)-acetonitrile as light brown crystals (90% yield based on 2-chloropyridine).

B. α-Phenyl-α-pyridyl-(2)-acetamide

| Materials: | |
|---|---|
| α-Phenyl-α-pyridyl-(2)-acetonitrile | 264 g (1.362 moles) |
| Conc. H$_2$SO$_4$ | 0.33 L (6.226 moles) |
| Water | 0.98 L |
| 50% NaOH | 0.77 L |

Procedure

The reactor was charged with conc. H$_2$SO$_4$, and cooled to ~10° C. α-Phenyl-α-pyridyl-(2)-acetonitrile (from Example 2.A) was added portionwise, keeping the to temperature below 30° C. The reaction was stirred at ambient temperature for 16 h. The reaction mixture then was cooled to 10° C., the water was added, and the NaOH was added to a pH of 12, keeping the temperature below 30° C. The resulting crystals were filtered, the filter cake was washed with water, and dried under vacuum to give 289 g (100%) of α-phenyl-α-pyridyl-(2)-acetamide.

C. d,l-erythro/threo-α-Phenyl-α-piperidyl-(2)-acetamide

| Materials: | |
|---|---|
| α-Phenyl-α-pyridyl-(2)-acetamide | 289 g (1.365 moles) |
| Platinum oxide (PtO$_2$) | 4.84 g |
| Acetic acid | 1.01 + 2.48 L |
| Celite | 300 + 150 g |

-continued

| Materials: | |
|---|---|
| Water | 2.48 + 0.62 + 1.24 L |
| 50% NaOH | 0.33 L |

Procedure

The reactor was charged with α-phenyl-α-pyridyl-(2)-acetamide (from Example 2. B), acetic acid (1.01 L), and PtO$_2$. The reactor then was filled with hydrogen gas, pressurized to 60 psi, and the mixture hydrogenated at room temperature for 16 h. The reaction mixture then was filtered through a pad of Celite (300 g) to remove the catalyst, and the Celite pad is washed with acetic acid (2.48 L). The filtrate was concentrated under reduced pressure. The resulting residue was dissolved in water (2.48 L), filtered through a pad of Celite (150 g), and the Celite pad was washed with water (0.62 L). The resulting filtrate was cooled to 10° C., followed by addition of 50% NaOH until the pH of the mixture was 13 and the free amine crystallized out. The crystals were filtered, washed with water (1.24 L), and dried to give 297 g (100%) of a 4:1 mixture of d,l-erythro-α-phenyl-α-piperidyl-(2)-acetamide and d,l-threo-α-phenyl-α-piperidyl-(2)-acetamide.

D. d,l-threo-α-Phenyl-α-piperidyl-(2)-acetamide

| Materials: | |
|---|---|
| Mixture of d,l-erythro-acetamide and d,l-threo-acetamide | 297 g (1.36 moles) |
| Potassium t-butoxide (95%) | 354 g (2.996 moles) |
| Toluene | 8.92 L |
| Water | 1.49 + 0.74 + 3.00 L |
| Conc. HCl | 0.59 + 0.30 L |
| 50% NaOH | 0.36 L |

Procedure

A mixture of d,l-erythro-acetamide and d,l-threo-acetamide (from Example 2.C), potassium t-butoxide, and toluene was heated to 70° C. and stirred for 16 h. The reaction mixture was cooled to room temperature, followed by slow addition of water (1.49 L). Conc. HCl (0.59 L) was added to this resulting mixture, which was stirred for 0.5 h. The layers were separated, and the top organic layer was then washed with a prepared solution of conc. HCl (0.30 L) and water (0.74 L). The combined aqueous layers were cooled to 10° C., and 50% NaOH was added to a pH of 12 whereby the free base precipitated out. The crystals were filtered, washed with water (3.00 L.), and dried to give 253 g (85%) of d,l-threo-α-phenyl-α-piperidyl-(2)-acetamide.

E. d-threo-α-Phenyl-α-piperidyl-(2)-acetamide

| Materials: | |
|---|---|
| d,l-threo-α-phenyl-α-piperidyl-(2)-acetamide | 253 g (1.159 moles) |
| Dibenzoyl-D-tartaric acid | 415 g (1.159 moles) |
| Isopropanol | 8.11 L |
| 6N HCl (aqueous) | 1.67 L |
| Water | 1.0 L |
| Solid NaCl | 290 g |
| 50% NaOH (aqueous) | 1.0 L |

Procedure

Dibenzoyl-D-tartaric acid and d,l-threo-α-phenyl-α-piperidyl-(2)-acetamide (from Example 2.D) were dissolved in isopropanol by warming the reaction mixture to ~50° C. The resulting clear solution was stirred at ambient temperature for 16 h, whereby the tartrate salt of d-threo-acetamide crystallized out. The crystals were filtered, and the filter cake was washed with isopropanol and dried in a vacuum oven at 40° C. This tartrate salt was added in portions to a stirred solution of 6N aq. HCl, and the resultant slurry was stirred at ambient temperature for 4 h. The slurry was filtered, and the filter cake (containing free dibenzoyl-D-tartaric acid) was washed with water. Solid NaCl was added to the filtrate (which contained d-threo-acetamide hydrochloride salt) and the mixture was cooled to ~10° C. The NaOH was added to this mixture to a pH of 12, whereby the free base of d-threo-acetamide precipitated out. The precipitated crystals were filtered, washed with water and dried to give 101 g (40%) of d-threo-α-phenyl-α-piperidyl-(2)-acetamide.

F. d-threo-Methylphenidate Hydrochloride

| Materials: | |
|---|---|
| d-threo-α-phenyl-α-piperidyl-(2)-acetamide | 101 g (0.46 moles) |
| Conc. H$_2$SO$_4$ | 121 mL |
| Methanol | 1.1 L |
| Water | 0.81 L |
| 50% NaOH | 175 mL |
| Diethyl ether | 1.0 + 1.0 + 1.0 + 1.0 L |
| Magnesium sulfate | 20 g |
| HCl gas | As needed. |

Procedure

A solution of d-threo-α-phenyl-α-piperidyl-(2)-acetamide (from Example 2.E) and conc. H$_2$SO$_4$ in methanol was heated to reflux and stirred for 2 days. The reaction mixture was cooled to room temperature and concentrated under reduced pressure. Water (0.81 L) and ether (1.0 L) were added to the residue. The NaOH was added to a pH of 12, and the layers were separated. The aqueous layer was extracted with ether (1.0 L). MgSO$_4$ was added to the combined ether layers, filtered, and washed with ether (1.0 L). HCl gas was passed through the filtrate with stirring, whereby white crystals of d-threo-methylphenidate hydrochloride precipitated out. The crystals were filtered, washed with ether (1.0 L), and dried to give 100 g (80%) of d-threo-methylphenidate hydrochloride.

In contrast to Example 1, the overall yield for Example 2 was 24.5%, an increase of over 66%.

EXAMPLE 3

Preparation of l-Threo-methylphenidate Hydrochloride Via Epimerization and Resolution of d,l-Threo-amide Enantiomers A. α-Phenyl-α-pyridyl-2-acetonitrile

| Materials: | |
|---|---|
| 2-Chloropyridine (99%) | 172 g (1.50 moles) |
| Benzyl cyanide (98%) | 188 g (1.576 moles) |
| Sodium amide (90%) | 130 g (3.00 moles) |
| Toluene | 0.59 + 0.10 L |
| Water | 0.52 L |
| Ethyl acetate | 0.26 L |
| Hexanes | 0.94 + 1.17 L |
| Brine | 0.26 L |

Procedure

The reactor was charged with 2-chloropyridine, benzyl cyanide, and toluene (0.59 L). Sodium amide powder was added over a 1 h period via a solid-addition funnel, keeping the reaction temperature below 300° C. The reaction mixture was stirred for 16 h at ambient temperature. The reaction was cooled to ~10° C., and quenched with 0.52 L water. Ethyl acetate (0.26 L) was added to solubilize the precipitated product. The organic layer was separated and washed once with 0.26 L brine, and solvent was removed from the organic layer on a rotovap. Toluene (0.10 L), followed by hexanes (0.94 L) were added to the resulting residue. The resulting slurry was filtered, and the filter cake was washed with hexanes (1.17 L), and dried to give 265 g of α-phenyl-α-pyridyl-(2)-acetonitrile as light brown crystals (90% yield based on 2-chloropyridine).

B. α-Phenyl-α-pyridyl-(2)-acetamide

| Materials: | |
| --- | --- |
| α-Phenyl-α-pyridyl-(2)-acetonitrile | 264 g (1.362 moles) |
| Conc. $H_2SO_4$ | 0.33 L (6.226 moles) |
| Water | 0.98 L |
| 50% NaOH | 0.77 L |

Procedure

The reactor was charged with conc. $H_2SO_4$, and cooled to ~10° C. α-Phenyl-α-pyridyl-(2)-acetonitrile (from Example 3.A) was added portionwise, keeping the temperature below 30° C. The reaction was stirred at ambient temperature for 16 h. The reaction mixture then was cooled to 10° C., the water was added, and the NaOH was added to a pH of 12, keeping the temperature below 30° C. The resulting crystals were filtered, the filter cake was washed with water, and dried under vacuum to give 289 g (100%) of α-phenyl-α-pyridyl-(2)-acetamide.

C. d,l-erythro/threo-α-Phenyl-α-piperidyl-(2)-acetamide

| Materials: | |
| --- | --- |
| α-Phenyl-α-pyridyl-(2)-acetamide | 289 g (1.365 moles) |
| Platinum oxide ($PtO_2$) | 4.84 g |
| Acetic acid | 1.01 + 2.48 L |
| Celite | 300 + 150 g |
| Water | 2.48 + 0.62 + 1.24 L |
| 50% NaOH | 0.33 L |

Procedure

The reactor was charged with α-phenyl-α-pyridyl-(2)-acetamide (from Example 3.B), acetic acid (1.01 L), and PtO2. The reactor then was filled with hydrogen gas, pressurized to 60 psi, and the mixture hydrogenated at room temperature for 16 h. The reaction mixture then was filtered through a pad of Celite (300 g) to remove the catalyst, and the Celite pad is washed with acetic acid (2.48 L). The filtrate was concentrated under reduced pressure. The resulting residue was dissolved in water (2.48 L), filtered through a pad of Celite (150 g), and the Celite pad was washed with water (0.62 L). The resulting filtrate was cooled to 10° C., followed by addition of 50% NaOH until the pH of the mixture was 13 and the fee amine crystallized out. The crystals were filtered, washed with water (1.24 L), and dried to give 297 g (100%) of a 4:1 mixture of d,l-erythro-α-phenyl-α-piperidyl-(2)-acetamide and d,l-threo-α-phenyl-α-piperidyl-(2)-acetamide.

D. d,l-threo-α-Phenyl-α-piperidyl-(2)-acetamide

| Materials: | |
| --- | --- |
| Mixture of d,l-erythro-acetamide and d,l-threo-acetamide | 297 g (1.36 moles) |
| Potassium t-butoxide (95%) | 354 g (2.996 moles) |
| Toluene | 8.92 L |
| Water | 1.49 + 0.74 + 3.00 L |
| Conc. HCl | 0.59 + 0.30 L |
| 50% NaOH | 0.36 L |

Procedure

A mixture of d,l-erythro-acetamide and d,l-threo-acetamide (from Example 3.C), potassium t-butoxide, and toluene was heated to 70° C. and stirred for 16 h. The reaction mixture was cooled to room temperature, followed by slow addition of water (1.49 L). Conc. HCl (0.59 L) was added to this resulting mixture, which was stirred for 0.5 h. The layers were separated, and the top organic layer was then washed with a prepared solution of conc. HCl (0.30 L) and water (0.74 L). The combined aqueous layers were cooled to 10° C., and 50% NaOH was added to a pH of 12 whereby the free base precipitated out. The crystals were filtered, washed with water (3.00 L), and dried to give 253 g (85%) of d,l-threo-α-phenyl-α-piperidyl-(2)-acetamide.

E. l-threo-α-Phenyl-α-piperidyl-(2)-acetamide

| Materials: | |
| --- | --- |
| d,l-threo-α-phenyl-α-piperidyl-(2)-acetamide | 253 g (1.159 moles) |
| Dibenzoyl-L-tartaric acid | 415 g (1.159 moles) |
| Isopropanol | 8.11 L |
| 6N HCl (aqueous) | 1.67 L |
| Water | 1.0 L |
| Solid NaCl | 290 g |
| 50% NaOH (aqueous) | 1.0 L |

Procedure

Dibenzoyl-L-tartaric acid and d,l-threo-α-phenyl-α-piperidyl-(2)-acetamide (from Example 3.D) is dissolved in isopropanol by warming the reaction mixture to ~50° C. The resulting clear solution is stirred at ambient temperature for 16 h, whereby the tartrate salt of l-threo-acetamide crystallizes out. The crystals are filtered, and the filter cake washed with isopropanol and dried in a vacuum oven at 40° C. This tartrate salt is added in portions to a stirred solution of 6N aq. HCl, and the resultant slurry is stirred at ambient temperature for 4 h. The slurry is filtered, and the filter cake (containing free dibenzoyl-L-tartaric acid) is washed with water. Solid NaCl is added to the filtrate (which contains l-threo-acetamide hydrochloride salt) and the mixture is cooled to ~10° C. The NaOH is added to this mixture to a pH of 12, whereby the free base of l-threo-acetamide precipitates out. The precipitated crystals are filtered, washed with water and dried to give l-threo-α-phenylα-piperidyl-(2)-acetamide.

F. l-threo-Methylphenidate Hydrochloride

| Materials: | |
| --- | --- |
| l-threo-α-phenyl-α-piperidyl-(2)-acetamide | 101 g (0.46 moles) |
| Conc. $H_2SO_4$ | 121 mL |

-continued

Materials:

| | |
|---|---|
| Methanol | 1.1 L |
| Water | 0.81 L |
| 50% NaOH | 175 mL |
| Diethyl ether | 1.0 + 1.0 1.0 + 1.0 L |
| Magnesium sulfate | 20 g |
| HCl gas | As needed. |

Procedure

A solution of l-threo-α-phenylα-piperidyl-(2)-acetamide (from Example 3.E) and conc. $H_2SO_4$ in methanol is heated to reflux and stirred for 2 days. The reaction mixture is cooled to room temperature and concentrated under reduced pressure. Water (0.81 L) and ether (1.0 L) are added to the residue. The NaOH is added to a pH of 12, and the layers are separated. The aqueous layer is extracted with ether (1.0 L). $MgSO_4$ is added to the combined ether layers, filtered, and washed with ether (1.0 L). HCl gas is passed through the filtrate with stirring, whereby white crystals of l-threo-methylphenidate hydrochloride precipitate out. The crystals are filtered, washed with ether (1.0 L), and dried to give l-threo-methylphenidate hydrochloride.

Those skilled in the art will appreciate that numerous changes and modifications may be made to the preferred embodiments of the present invention and that such changes and modifications may be made without departing from the spirit of the invention. It is therefore intended that the appended claims cover all such equivalent variations as fall within the true spirit and scope of the invention.

What is claimed is:

1. A synthetic process for preferentially forming d-threo acid salts of d-threo piperidyl acetamide stereoisomers with respect to l-threo piperidyl acetamide stereoisomers comprising the steps of:

providing a mixture of said d,l-threo piperidyl acetamide stereoisomers having formulas:

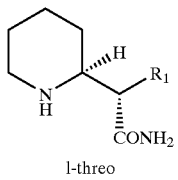 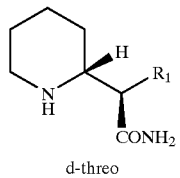
l-threo          d-threo wherein $R_1$ is aryl having about 6 to about 28 carbon atoms;

reacting said stereoisomers with an acid resolving agent in an organic solvent, thereby forming acid salts;

precipitating said acid salts; and isolating said acid salts.

2. The process of claim 1 wherein $R_1$ is phenyl.

3. The process of claim 1 wherein said solvent comprises an alcohol, an alkyl alkanoate, a ketone, or an ether.

4. The process of claim 1 wherein said solvent is an alkyl alcohol having 1 to about 5 carbon atoms.

5. The process of claim 1 wherein said alkyl alcohol is isopropanol.

6. The process of claim 1 wherein said acid resolving agent is a derivative of D-tartaric acid.

7. The process of claim 1 wherein said acid resolving agent is a tartaric acid derivative having formula $HO_2CCH[OC(O)R_3]CH[OC(O)R_3]CO_2H$ wherein each $R_3$, independently, is aryl having 6 to about 28 carbon atoms or aralkyl having 7 to about 28 carbon atoms.

8. The process of claim 7 wherein $R_3$ is aralkyl having 7 to about 28 carbon atoms.

9. The process of claim 1 further comprising reacting said d-threo acid salts with aqueous base to form said d-threo piperidine acetamide.

10. The process of claim 9 further comprising reacting said d-threo piperidine acetamide with an alcohol having 1 to about 5 carbon atoms in the presence of acid to form a d-threo piperidine acetate.

11. The process of claim 1 wherein said d,l-threo piperidyl acetamide stereoisomers are prepared by reacting a pyridine having formula:

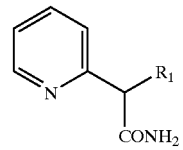

with hydrogen in an alkanoic acid having 1 to about 10 carbon atoms in the presence of a catalyst to provide a mixture of threo and erythro piperidyl stereoisomers; and contacting said erythro stereoisomers with organic base, thereby converting said erythro piperidyl stereoisomers to threo piperidyl stereoisomers.

12. The product of the process of claim 1.

* * * * *

UNITED STATES PATENT AND TRADEMARK OFFICE
CERTIFICATE OF CORRECTION

PATENT NO. : 6,962,997 B1
DATED : November 8, 2005
INVENTOR(S) : Khetani et al.

It is certified that error appears in the above-identified patent and that said Letters Patent is hereby corrected as shown below:

<u>Title page,</u>
Item [56], References Cited, OTHER PUBLICATIONS,
"Morrison & Byd" reference, delete "Orgainc" and replace with -- Organic --.
"Vanderplas et al." reference, delete "cis-benayl-" and insert -- cis-benzyl- --.

<u>Column 12,</u>
Line 57, delete "-phenylα-" and replace with -- -phenyl-α- --.

<u>Column 13,</u>
Line 12, delete "-phenylα-" and replace with -- -phenyl-α- --.

Signed and Sealed this

Eighteenth Day of April, 2006

JON W. DUDAS
*Director of the United States Patent and Trademark Office*